US011311592B2

United States Patent
Huang et al.

(10) Patent No.: US 11,311,592 B2
(45) Date of Patent: Apr. 26, 2022

(54) *BAUHINIA* EXTRACT AND USES THEREOF

(71) Applicants: Academia Sinica, Taipei (TW); Industrial Technology Research Institute, Hsin Chu (TW)

(72) Inventors: Chang-Jen Huang, Taipei (TW); Rita P.-Y. Chen, Taipei (TW); Yung-Feng Liao, Taipei (TW); Bo-Kai Wu, Taipei (TW); Po-Ting Chen, Taipei (TW); Hui-Ping Tsai, Hsinchu (TW); Yi-Cheng Cheng, Hsinchu (TW); Cheng-Li Fang, Hsinchu (TW); Hung-Chi Chien, Hsinchu (TW); Tien-Soung Tong, Hsinchu (TW); Ting-Shou Chen, Hsinchu (TW); Shu-Jiau Chiou, Hsinchu (TW)

(73) Assignees: ACADEMIA SINICA, Taipei (TW); INDUSTRIAL TECHNOLOGY RESEARCH INSTITUTE, Hsin Chu (TW)

(*) Notice: Subject to any disclaimer, the term of this patent is extended or adjusted under 35 U.S.C. 154(b) by 166 days.

(21) Appl. No.: 16/799,158

(22) Filed: Feb. 24, 2020

(65) Prior Publication Data
US 2020/0246410 A1 Aug. 6, 2020

Related U.S. Application Data

(62) Division of application No. 15/772,810, filed as application No. PCT/US2016/060359 on Nov. 3, 2016, now Pat. No. 10,610,557.

(Continued)

(51) Int. Cl.
*B01D 11/02* (2006.01)
*A61K 36/48* (2006.01)
(Continued)

(52) U.S. Cl.
CPC ............ *A61K 36/48* (2013.01); *A61K 9/0053* (2013.01); *A61P 25/28* (2018.01); *A61K 2236/00* (2013.01);
(Continued)

(58) Field of Classification Search
CPC ................................................. B01D 11/0288
See application file for complete search history.

(56) References Cited

U.S. PATENT DOCUMENTS

2009/0169585 A1 7/2009 Sardi
2014/0134283 A1 5/2014 Geissler et al.

FOREIGN PATENT DOCUMENTS

| BR | P10903215-0 A2 | 4/2011 |
| CN | 104857079 A | 8/2015 |
| WO | WO-03011311 A1 | 2/2003 |

OTHER PUBLICATIONS

Koti et al., "Effect of Bauhinia variegata bark extract on blood glucose level in normal and alloxanised diabetic rats," Journal of Natural Remedies 9(1):27-34, 2009.*

(Continued)

*Primary Examiner* — Rosanne Kosson
(74) *Attorney, Agent, or Firm* — Muncy, Geissler, Olds & Lowe, P.C.

(57) ABSTRACT

Disclosed herein is the novel use of use of a *Bauhinia* spp. extract, which may upregulate neprilysin, induce autophagy, protect neuron from amyloidopathy or tauopathy, and/or promote neurite outgrowth, thus the *Bauhinia* spp. extract of the present disclosure may be used as a dietary supplement (Continued)

for the prophylaxis or treatment of amyloid related neurodegenerative diseases so as to ameliorate or alleviate symptoms associated with the amyloid related neurodegenerative diseases.

5 Claims, 9 Drawing Sheets

Specification includes a Sequence Listing.

Related U.S. Application Data

(60) Provisional application No. 62/251,638, filed on Nov. 5, 2015.

(51) Int. Cl.
*A61P 25/28* (2006.01)
*A61K 9/00* (2006.01)

(52) U.S. Cl.
CPC .. *A61K 2236/331* (2013.01); *A61K 2236/333* (2013.01)

(56) References Cited

OTHER PUBLICATIONS

Kim et al., "SIRT1 deacetylase protects against neurodegeneration in models for Alzheimer's disease and amyotrophic lateral sclerosis," The EMBO Journal, 2007, vol. 26, pp. 3169-3176, 11 pages.

Nemalapalli et al., "Effect of ethanolic seed extract of *Bauhinia purpurea* linn on cognition in scopolamine induced Alzheimer's disease rat's model," Journal of Comprehensive Pharmacy, 2015 2(4), pp. 145-150, 6 pages.

Jatav et al., "Nootropic potential of *Bauhinia variegata*: A systematic study on murine model," Archives of Medicine and Health Sciences, vol. 2, Issue 1, 2014, pp. 29-35, 7 pages.

Mali et al., "Mast Cell Stabilizing Activity of *Bauhinia variegata*," Journal of Herbs, Spices & Medicinal Plants, 17, 2011, pp. 268-274, 7 pages.

Pani et al., "Nephroprotective effect of *Bauhinia variegata* (Linn.) whole stem extract against cisplatin-induced nephropathy in rats," Indian Journal of Pharmacology, Apr. 2011, 43(2), pp. 200-202, 3 pages.

\* cited by examiner

A. Spatial Acquisition Trial

B. Probe Trial

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: synthetic, primer for APPswe

<400> SEQUENCE: 1
aggactgacc actcgaccag                                           20

<210> SEQ ID NO 2
<211> LENGTH: 19
<212> TYPE: DNA

```
<213> ORGANISM: Artificial Sequence
<220> FEATURE:
<223> OTHER INFORMATION: synthetic, primer for APPswe

<400> SEQUENCE: 2
cgggggtcta gttctgcat                                                    19

<210> SEQ ID NO 3
<211> LENGTH: 20
<212> TYPE: DNA
<213> ORGANISM: Artificial Sequence
<220> FEATURE:
<223> OTHER INFORMATION: synthetic, primer for PSEN1dE9

<400> SEQUENCE: 3
aatagagaac ggcaggagca                                                   20

<210> SEQ ID NO 4
<211> LENGTH: 19
<212> TYPE: DNA
<213> ORGANISM: Artificial Sequence
<220> FEATURE:
<223> OTHER INFORMATION: synthetic, primer for PSEN1dE9

<400> SEQUENCE: 4
gccatgaggc actaatcat                                                    19
```

BAUHINIA EXTRACT AND USES THEREOF

CROSS-REFERENCE TO RELATED APPLICATIONS

This application is a divisional application of U.S. application Ser. No. 15/772,810, filed May 1, 2018, which is an application U.S. National Stage Filing under 35 U.S.C. 371 from International Patent Application Serial No. PCT/US2016/060359, filed Nov. 3, 2016, and published on May 11, 2017, which claims the priority of U.S. Ser. No. 62/251,638, filed Nov. 5, 2015, the disclosure of which are incorporated by reference herein in their entireties.

BACKGROUND OF THE INVENTION

1. Field of the Invention

The present disclosure relates in general, to the novel use of a *Bauhinia* spp. extract. More specifically, the present disclosure relates to the use of *Bauhinia* spp. extract as a dietary supplement for the treatment of a neurodegenerative disease.

2. Description of Related Art

*Bauhinia variegata* Linn. (Fabaceae) is traditionally prescribed in indigenous medicines in India. Various parts of the plant (flower buds, flowers, stem, stem bark, leaves, seeds, and roots) are used in the treatment of asthma, jaundice, tuberculosis, leprosy, and skin diseases. It has also been reported that the stem bark of *B. variegata* possess antitumor, anti-ulcer, and antibacterial activities. Recent studies in animal models further demonstrated that the ethanol extract of *B. variegata* (BVEE) exhibited significant nephroprotective effect against cisplatin-induced nephropathy, and antidiabetic activity in alloxan-induced hyperglycemic activities.

Alzheimer's disease (AD) is a progressive neurodegenerative disease and is the most prevalent form of age-related dementia. It is widely believed that the accumulation of Aβ and Tau in AD is the causative event triggering neurodegeneration and related pathogenic pathways, which together contribute to the onset and progression of AD. The truncation of Tau protein has been identified in human sporadic AD, and could also instigate the aggregation of Tau and formation of neurofibrillary tangles in AD. Accumulated evidence indicated that neprilysin (NEP) is the primary endopeptidase responsible for the clearance of Aβ and that its functional deficiency is evident during aging process and AD. Consistent with this notion, an inverse correlation is observed between NEP levels and brain Aβ loads in NEP knock-out mice (20-24). NEP has thus been regarded as the most promising pharmacological target for the development of therapeutics aiming to promote Aβ degradation as AD treatments (25-30). Furthermore, autophagic vacuoles has been shown to be the major intracellular compartment for Tau clearance. This autophagy-mediated degradation system is also believed to play a significant role in controlling the homeostasis of Aβ. Consistent with its protective role in neurons, defective autophagy has been implicated in the pathogenesis of various neurodegenerative diseases, including AD. Emerging findings suggest that autophagosomes can engulf damaged organelles and aberrant protein aggregates for the clearance of these internalized cargos following fusion with lysosomes. It is thus reasonable to speculate that autophagy-inducing agents could render neuroprotective efficacy through promoting the autophagy-mediated clearance of aberrant protein aggregates, including Aβ and Tau.

By use of a zebrafish model of tauopathy, a cell-based assay for neprilysin, and a cell-based assay for autophagy, inventors of the present disclosure unexpectedly discovered that *Bauhinia* spp. extract can simultaneously inhibit tauopathy-elicited neurotoxicity, enhance neprilysin activity, and induce autophagic activity, thus the present identified *Bauhinia* spp. extract could be used as a health food dietary supplements to improve overall memory and/or cognitive function of a patient suffering from a neurodegenerative disease.

SUMMARY

The present disclosure relates to novel use of a *Bauhinia* spp. extract in upregulating neprilysin, inducing autophagy, protecting neuron from amyloidopathy or tauopathy, and/or promoting neurite outgrowth, thus the *Bauhinia* spp. extract of the present disclosure may be used as a dietary supplement for the prophylaxis or treatment of amyloid related neurodegenerative diseases so as to ameliorate or alleviate symptoms associated with the amyloid related neurodegenerative diseases.

Accordingly, it is the first aspect of the present disclosure to provide a method for the treatment of a subject having or suspected of having an amyloid related neurodegenerative disease. The method includes the step of, orally administering to the subject a therapeutically effective amount of a *Bauhinia* spp. extract to ameliorate or alleviate symptoms associated with the amyloid related neurodegenerative diseases.

According to embodiments of the present disclosure, the *Bauhinia* spp. may be *Bauhinia variegate* or *Bauhiniaxblakeana*.

According to embodiments of the present disclosure, the *Bauhinia* spp. extract may be a water extract or an ethanol extract.

According to some embodiments of the present disclosure, the water extract of *Bauhinia* spp. is produced by mixing the powdered stem of *Bauhinia* spp. with water at a ratio of 1:5 (w/v) to 1:20 (w/v) at about 30-100° C. for about 0.5-5 hrs. Preferably, the water extract of *Bauhinia* spp. is produced by mixing the powdered stem of *Bauhinia* spp. with water at a ratio of 1:10 (w/v) at about 50° C. for about 2 hrs.

According to further embodiments of the present disclosure, the ethanol extract of *Bauhinia* spp. is produced by mixing the powdered stem of *Bauhinia* spp. with 95% ethanol (vol %) at a ratio of 1:5 (w/v) to 1:20 (w/v) at about 15-35° C. for about 1-10 days. Preferably, the ethanol extract of *Bauhinia* spp. is produced by mixing the powdered stem of *Bauhinia* spp. with 95% ethanol (vol %) at a ratio of 1:10 (w/v) at about 25° C. for about 7 days.

According to embodiments of the present disclosure, the *Bauhinia* spp. extract is orally administered to the subject in the amount of about 5-50 mg/Kg. Preferably, the *Bauhinia* spp. extract is orally administered to the subject in the amount of about 20 mg/Kg.

According to embodiments of the present disclosure, the neurodegenerative disease that may be treated by the present *Bauhinia* spp. extract is selected from the group consisting of, Alzheimer's disease (AD), Huntington's disease (HD), vascular dementia, frontotemporal dementia, semantic dementia and dementia with Lewy bodies, amyolateral sclerosis (ALS), and Parkinson's disease (PD).

The details of one or more embodiments of the invention are set forth in the accompanying description below. Other features and advantages of the invention will be apparent from the detail descriptions, and from claims.

BRIEF DESCRIPTION OF THE DRAWINGS

The present description will be better understood from the following detailed description read in light of the accompanying drawings, where.

Figure 1:
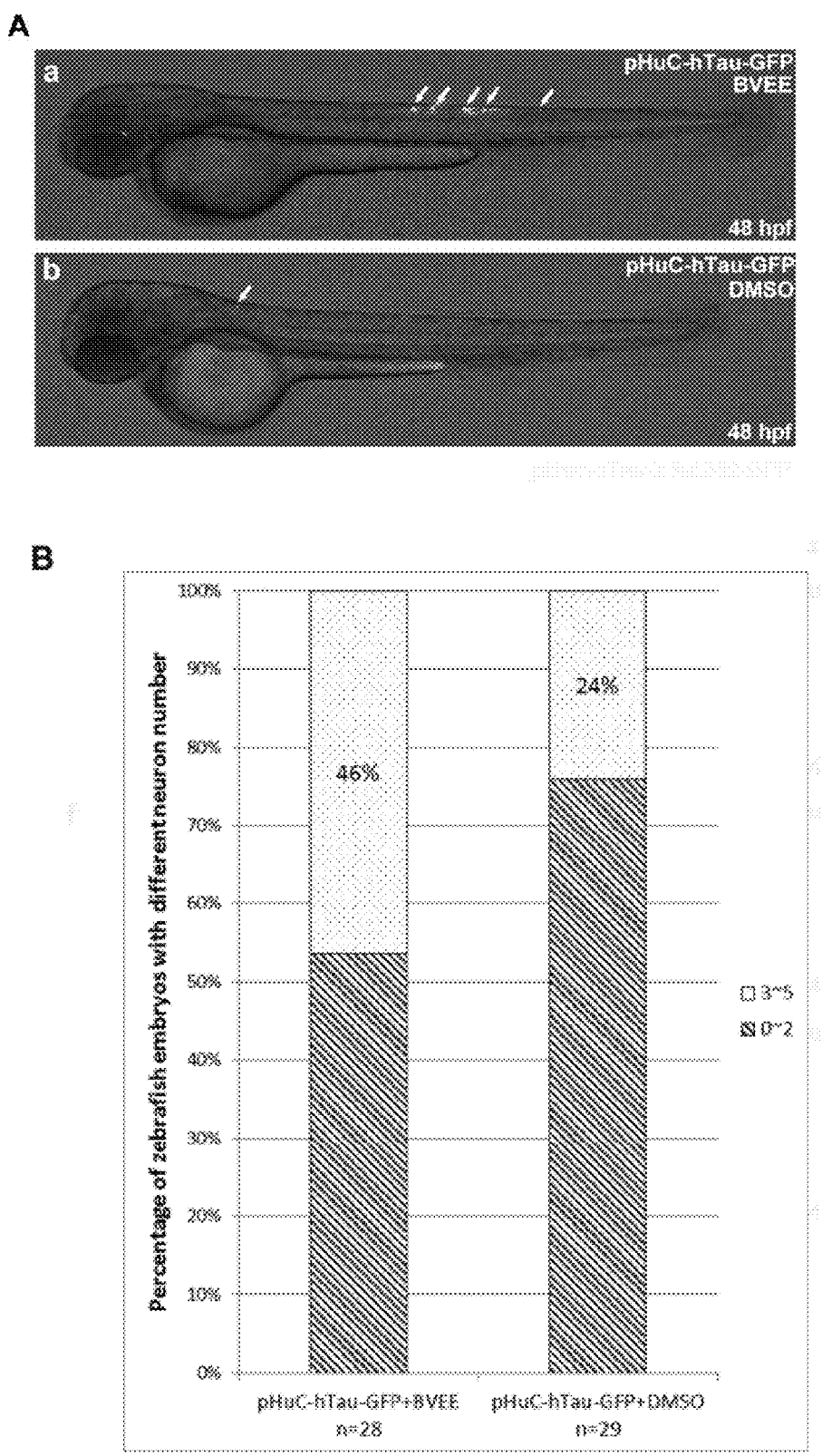
FIG. 1. Treatment of *Bauhinia* extract could decrease neuronal death by overexpression of human tau-GFP in zebrafish embryo. A. The expression construct pHuC-hTau-GFP was first injected into zebrafish embryos at 1-cell stage. Then, GFP-labeled neuronal cells were observed at 24, 48 and 72 hpf. Some GFP signals were observed in neuronal cells of 24 hpf embryos, then broken down as small dots and diminished in 48 hpf embryos. However, there were other GFP signals remained intact in neuronal cells. B. Neuronal numbers with GFP signals in embryos at 48 hpf were counted and separated into two groups, lower than 2 neurons (0-2) and more neurons between 3-5. Treatment of BVEE enhanced embryos with more neurons (FIG. 1, panel a) with 46% (FIG. 1, panel B)

The p62-RL-HEK cells were treated with or without *B. variegate* extract (50 mg/ml) at 37° C. for 24 h. Additional treatments with either rapamycin (RAP) or 3-MA were included as references. *Renilla* luciferase (Luc) activity was determined by the addition of coelenterazine to a final concentration of 5 mM. Luminescence emitted by DMSO-treated cells (Control) was referred to as 100% relative *Renilla* luciferase signal. Extracts derived from different solvents were lyophilized, and redissolved in DMSO for subsequent analysis. Capital letter denotes the solvent used in the extraction of *B. variegate*. A, hexane; B, ether; C, ethyl acetate; D, hot water; E, ethanol.

DESCRIPTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

1. Definitions

For convenience, certain terms employed in the context of the present disclosure are collected here. Unless defined otherwise, all technical and scientific terms used herein have the same meaning as commonly understood by one of the ordinary skill in the art to which this invention belongs.

Unless otherwise defined herein, scientific and technical terminologies employed in the present disclosure shall have the meanings that are commonly understood and used by one of ordinary skill in the art. Unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques. Ranges can be expressed herein as from one endpoint to another endpoint or between two endpoints. All ranges disclosed herein are inclusive of the endpoints, unless specified otherwise.

The term "treatment" as used herein includes preventative (e.g., prophylactic), curative or palliative treatment; and "treating" as used herein also includes preventative (e.g., prophylactic), curative or palliative treatment. In particular, the term "treating" as used herein refers to the application or administration of the present molecular construct or a pharmaceutical composition comprising the same to a subject, who has a medical condition a symptom associated with the medical condition, a disease or disorder secondary to the medical condition, or a predisposition toward the medical condition, with the purpose to partially or completely alleviate, ameliorate, relieve, delay onset of, inhibit progression of, reduce severity of, and/or reduce incidence of one or more symptoms or features of said particular disease, disorder, and/or condition. Treatment may be administered to a subject who does not exhibit signs of a disease, disorder and/or condition, and/or to a subject who exhibits only early signs of a disease, disorder and/or condition, for the purpose of decreasing the risk of developing pathology associated with the disease, disorder and/or condition.

The term "therapeutically effective amount" as used herein refers to the quantity of the present recombinant protein that is sufficient to yield a desired therapeutic response. A therapeutically effective amount of an agent is not required to cure a disease or condition but will provide a treatment for a disease or condition such that the onset of the disease or condition is delayed, hindered or prevented, or the disease or condition symptoms are ameliorated. The therapeutically effective amount may be divided into one, two or more doses in a suitable form to be administered at one, two or more times throughout a designated time period. The specific effective or sufficient amount will vary with such factors as the particular condition being treated, the physical condition of the patient (e.g., the patient's body mass, age, or gender), the type of mammal or animal being treated, the duration of the treatment, the nature of concurrent therapy (if any), and the specific formulations employed and the structure of the compounds or its derivatives. The therapeutically effective amount may be expressed, for example, as the total mass of the drug, i.e., the *Bauhinia* spp. extract in grams, milligrams or micrograms; or a ratio of mass of the drug to body mass, i.e., the *Bauhinia* spp. extract as milligrams per kilogram (mg/kg). Specifically, the term "therapeutically effective amount" used in connection with the *Bauhinia* spp. extract described herein refers to the quantity of the *Bauhinia* spp. extract, which is sufficient to upregulate neprilysin, induce autophagy, protect neuron from amyloidopathy or tauopathy, and/or promote neurite outgrowth, thereby alleviate or ameliorate the symptoms associated with the neurodegenerative disease in the subject. Persons having ordinary skills could calculate the human equivalent dose (HED) for the medicament (such as the compounds of the present disclosure) based on the doses determined from animal models set forth in the working examples of the present disclosure. For example, one may follow the guidance for industry published by US Food and Drug Administration (FDA) entitled "Estimating the Maximum Safe Starting Dose in Initial Clinical Trials for Therapeutics in Adult Healthy Volunteers" in estimating a maximum safe dosage for use in human subjects.

The terms "administering or administration" as used herein refers to the application of a *Bauhinia* spp. extract or a pharmaceutical composition comprising the same to a subject in need of a treatment thereof.

The terms "subject" and "patient" are used interchangeably herein and are intended to mean an animal including the human species that is treatable by the molecular construct, pharmaceutical composition and/or method of the present invention. The term "subject" or "patient" intended to refer to both the male and female gender unless one gender is specifically indicated. Accordingly, the term "subject" or "patient" comprises any mammal, which may benefit from the treatment method of the present disclosure. Examples of a "subject" or "patient" include, but are not limited to, a human, rat, mouse, guinea pig, monkey, pig, goat, cow, horse, dog, cat, bird and fowl. In an exemplary embodiment, the patient is a human. The term "mammal" refers to all members of the class Mammalia, including humans, primates, domestic and farm animals, such as rabbit, pig, sheep, and cattle; as well as zoo, sports or pet animals; and rodents, such as mouse and rat. The term "non-human mammal" refers to all members of the class Mammalis except human.

2. Preparation of Bauhinia Spp. Extract

The present invention is based on the discovery that the Bauhinia spp. extract prepared in according to procedures described in the working example of the present disclosure is capable of upregulating neprilysin, inducing autophagy, protecting neuron from amyloidopathy or tauopathy, and/or promoting neurite outgrowth, and exerts no toxic effects toward metabolite enzymes and/or renal functions, thereby may be used as a dietary supplement to alleviate or ameliorate the symptoms associated with a neurodegenerative disease in a subject in need of such treatment.

Accordingly, the first aspect of the present disclosure is to provide a Bauhinia spp. extract, which is useful for the treatment of a subject having or suspected of having a neurodegenerative disease.

Examples of suitable species of Bauhinia spp. for use in the present disclosure include, but are not limited to, Bauhinia variegate and Bauhiniax blakeana Dunn.

In one example, the Bauhinia spp. extract of the present disclosure is prepared from the fresh or dried powdered stem of Bauhinia variegate. In another example, the Bauhinia spp. extract of the present disclosure is prepared from the fresh or dried powdered stem of Bauhiniaxblakeana Dunn. According to embodiments of the present disclosure, the dried powdered stem of Bauhinia spp. is mixed with a non-toxic solvent in a ratio of about 1:5 (w/v) to 1:20 (w/v) at suitable temperature for various periods of time so as to produce an extract that contains active components, i.e., components that upregulate neprilysin (NEP) activity, or promote the neurite outgrowth.

According to some embodiments of the present disclosure, the present Bauhinia spp. extract is produced by mixing the powdered stem of Bauhinia spp. with water at a ratio of 1:5 (w/v) to 1:20 (w/v), such as 1:5, 1:6 1:7, 1:8, 1:10, 1:11, 1:12, 1:13, 1:14, 1:15, 1:16, 1:17, 1:18, 1:19, and 1:20 (w/v), at a temperature of about 30-100° C., such as 30, 40, 50, 60, 70, 80, 90, and 100° C. for a period of about 0.5-5 hrs, such as 0.5, 0.6, 0.7, 0.8, 0.9, 1, 2, 3, 4, and 5 hrs. Preferably, the Bauhinia spp. is produced by mixing the powdered stem of Bauhinia spp. with water at a ratio of 1:8 (w/v) to 1:15 (w/v), such as 1:8, 1:10, 1:11, 1:12, 1:13, 1:14, and 1:15, (w/v), at a temperature of about 40-80° C., such as 40, 50, 60, 70, and 80° C. for a period of about 1-3 hrs, such as 1, 2, and 3 hrs. Most preferably, the Bauhinia spp. is produced by mixing the powdered stem of Bauhinia spp. with water at a ratio of 1:10 (w/v) at about 50° C. for about 2 hrs.

According to other embodiments of the present disclosure, the present Bauhinia spp. extract is produced by mixing the powdered stem of Bauhinia spp. with 95% ethanol (vol %) at a ratio of 1:5 (w/v) to 1:20 (w/v), such as 1:5, 1:6 1:7, 1:8, 1:10, 1:11, 1:12, 1:13, 1:14, 1:15, 1:16, 1:17, 1:18, 1:19, and 1:20 (w/v), at a temperature of about 15-35° C., such as 15, 16, 17, 18, 19, 20, 21, 22, 23, 24, 25, 26, 27, 28, 29, 30, 31, 32, 33, 34, and 35° C. for about 1-10 days. Preferably, the present Bauhinia spp. extract is produced by mixing the powdered stem of Bauhinia spp. with 95% ethanol (vol %) at a ratio of 1:8 (w/v) to 1:15 (w/v), such as 1:8, 1:10, 1:11, 1:12, 1:13, 1:14, and 1:15 (w/v), at a temperature of about 20-30° C., such as 20, 21, 22, 23, 24, 25, 26, 27, 28, 29, and 30° C. for about 3-8 days. Most preferably, the present Bauhinia spp. extract is produced by mixing the powdered stem of Bauhinia spp. with 95% ethanol (vol %) at a ratio of 1:10 (w/v) at about 25° C. for about 7 days.

The Bauhinia spp. extract thus obtained is preferably freeze dried or lyophilized and stores in a cool, dry and light-proof environment until use.

3. Use of the Bauhinia Spp. Extract

According to embodiments of the present disclosure, the Bauhinia spp. extract prepared in accordance with the method of the present disclosure is capable of reducing tauopathy induced neuron toxicity (see Example 1), promoting neurite outgrowth (see Example 2), activating autophagy (see Example 3), and upregulating neprilysin (NEP) activity (see Example 4) in vitro; improving memory and cognitive functions (see Examples 6 and 7) in vivo. Most importantly, it does not impair metabolic enzyme activity or renal function (see Example 8), nor does it exert any cytotoxicity (see Example 5). Thus, the present Bauhinia spp. extract may be sued as a dietary supplement to treat a subject having a neurodegenerative disease, particularly an amyloid related neurodegenerative diseases, to improve the overall memory and cognitive functions of the subject.

Accordingly, it is the second aspect of the present disclosure to provide a method of treating a subject having or suspected of having a neurodegenerative disease. The method includes the step of, orally administering to the subject a therapeutically effective amount of the present Bauhinia spp. extract to ameliorate or alleviate symptoms associated with the amyloid related neurodegenerative diseases.

Examples of neurodegenerative disease that may be treated by the present Bauhinia spp. extract include but are not limited to, Alzheimer's disease (AD), Huntington's disease (HD), vascular dementia, frontotemporal dementia, semantic dementia and dementia with Lewy bodies, amyolateral sclerosis (ALS), and Parkinson's disease (PD).

The Bauhinia spp. extract useful with the present method may be a water extract or an ethanol (i.e., 95% ethanol) extract of Bauhinia variegate or Bauhiniaxlakeana. In some examples, the 95% ethanol extract of Bauhinia variegate is employed; whereas in other examples, the water extract of Bauhinia variegate or Bauhiniaxblakeana is preferred.

According to embodiments of the present disclosure, the Bauhinia spp. extract is orally administered to the subject in a single dose or in multiple doses (e.g., 2, 3 or 4 doses) at an amount of about 5-50 mg/Kg/day, such as 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50 mg/Kg/day. Preferably, the *Bauhinia* spp. extract is orally administered to the subject in the amount of about 10-40 mg/Kg/day, such as 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 and 40 mg/Kg/day. More preferably, the *Bauhinia* spp. extract is orally administered to the subject in the amount of about 15-35 mg/Kg/day, such as 15, 16, 17, 18, 19, 20, 21, 22, 23, 24, 25, 26, 27, 28, 29, 30, 31, 32, 33, 34, and 35 mg/Kg/day. Most preferably, the *Bauhinia* spp. extract is orally administered to the subject in the amount of about 20 mg/Kg/day.

The present *Bauhinia* spp. extract may be manufactured into dosage formulations suitable for oral administration, such as powders, tablets, caplets, capsules, solutions, and/or suspensions, by mixing suitable amounts of the lyophilized *Bauhinia* spp. extract with pharmaceutically acceptable excipients, binders, disintegrants, dispersants, diluents, lubricants, flavoring agents, and/or coloring agents to produce the desired oral formulations. For example, the dried granules of the present *Bauhinia* spp. extract may be directly compressed into pharmaceutically flash-melt oral dosage forms, e.g., tablets, caplets, and the like by mixing with suitable excipients. Alternatively, the dried granules of the present *Bauhinia* spp. extract may be encapsulated within gelatin capsules. Still optionally, the present *Bauhinia* spp. extract may be dissolved or suspended in a suitable solvent, such as water, a buffer solution or elixir to produce orally administered liquid or suspension.

The present invention will now be described more specifically with reference to the following embodiments, which are provided for the purpose of demonstration rather than limitation.

Examples

Materials and Methods
Preparation of Crude *Bauhinia* Extract
The air-dried, 100 g powdered stems of *B. variegate* (BV) or *Bauhinia×blakeana* Dunn. (BB) were extracted at a ratio of 1:10 (w/v) with 95% ethanol (BVEE or BBEE) on a rotary shaker (150 rpm) for 7 days at room temperature. Water extraction was carried out in $H_2O$ (1:10; w/v) for two hours at 50° C.

Extracts of *B. variegate* (BV) using organic solvents such as hexane, ether, and ethyl acetate (EA) were also prepared in similar fashion according to ethanol based extraction procedures. All the filtrates were lyophilized and stored at −20° C.

Cell Culture
Human embryonic kidney (HEK) cell line 293 and stable cell lines derived therefrom (GFP-LC3-HEK and p62-RL-HEK), as well as neuroblastoma cell line SH-SY5Y were cultured in minimum essential medium supplemented with 10% (v/v) heat-inactivated fetal bovine serum, 50% (v/v) F-12 nutrient mixture, and 1% (v/v) antibiotic mixture comprised of penicillin and streptomycin. Cells were kept at 37° C. in a humidified atmosphere of 5% $CO_2$. SH-SY5Y cells were plated at a density of $1×10^5$ viable cells per well in 96-well plates for future analysis.

Animals
C57BL16 male mice were purchased from the National Laboratorial Animal Center (Taipei, Taiwan, R.O.C.) and kept at the Experimental Animal Facility of the Institute of Cellular and Organismic Biology (ICOB) at Academia Sinica, in which each mice was housed in individually ventilated cage (IVC) with a 12:12 hr light-dark cycle with food and water provided ad libitum. Experimental procedures for the described animal study were approved by the Institutional Animal Care and Utilization Committee (IACUC) of Academia Sinica (Taipei, Taiwan, R.O.C.). Mice were.

Assay on Tauopathy Toxicity
The ability of wild-type human Tau protein to induce cell death in developing neuronal cells was investigated using GFP-hTau fusion protein under the control of neuron-specific HuC promoter (Park et al., 2000). The expression construct was injected into zebrafish embryos at 1-cell stage. GFP-labeled neuronal cells were observed at 24, 48 and 72 hpf by use of a fluorescence microscope. Some GFP signals were observed in neuronal cells of 24 hpf embryos, then broken down as small dots and diminished in 48 hpf embryos. However, there were other GFP signals remained intact in neuronal cells. Neuronal numbers with GFP signals in embryos at 72 hpf were counted and separated into two groups, lower than 2 neurons (0-2) and more neurons (between 3-5).

Assay on Neurite Outgrowth Activity
To test whether BVEE can promote neurite outgrowth in zebrafish embryos, the expression plasmid pHuC-GFP, in which the GFP protein was expressed under the control of a neuron-specific HuC promoter, was first injected into zebrafish embryos at one-cell stage. Eight hours after injection, those injected embryos were treated with BVEE or DMSO as control. Another 40 hr after treatment, zebrafish numbers with significant neurite outgrowth were counted.

Cell Viability Assay
HEK or derived stable cell lines (GFP-LC3-HEK and p62-RL-HEK) ($5×10^4$ cells/100 µL/well) were seeded onto each wells of 96-well microplates in culture medium containing respective compounds as specified and incubated at 37° C. for 24 hr. Viable cells were determined using the CellTiter 96 AQueous non-radioactive cell proliferation assay (Promega) in accordance with protocols described in the manufacturer's manual. Briefly, after the addition of the combined 3-(4,5-dimethylthiazol-2-yl)-5-(3-carboxymethoxyphenyl)-2-(4-sulfophenyl)-2H-tetra zolium, inner salt/phenazine methosulfate solution (20 µL/well), microplates were incubated for 3 hr at 37° C. The conversion of 3-(4,5-dimethylthiazol-2-yl)-5-(3-carboxymethoxyphenyl)-2-(4-sulfophenyl)-2H-tetra zolium, inner salt into formazan in viable cells was quantitated by the absorbance at 490 nm using a fluorescence/luminescence microplate reader (SpectraMax M5, Molecular Devices). The number of viable cells in culture was directly proportional to the absorbance at 490 nm. Viable cells in culture medium containing vehicle alone (0.1% DMSO, control) were referred to as 100% viability.

Cell-Based Reporter Assay for the Screening of Autophagy-Modulating Agents
To generate a cell-based p62 degradation assay specific for autophagic activity, stable clone of HEK cells (p62-RL-HEK) that constitutively express p62 C-terminally fused with *Renilla* luciferase reporter (p62-RL) was generated. The *Renilla* luciferase signal in p62-RL-HEK cells could thus be measured to determine the steady level of p62-RL in the cells. Our studies confirmed that the increase of luciferase signal was resulted from the inhibition of autophagy-mediated degradation of p62, while the decrease of luciferase signal was due to the induction of autophagy-mediated p62 degradation. The efficiency of this cell-based assay was evaluated by an autophagy inhibitor 3-methyladenine (3-MA) and an autophagy inducer rapamycin, respectively.

To identify effective herbal extracts that contain active ingredients of autophagy modulators, p62-RL-HEK cells ($2\times10^5$ cells/well) were seeded onto 96-well microplates and incubated at 37° C. for 2 days, followed by treatments with 200 μg/mL of individual herbal extract for 24 hr at 37° C. Luciferase signals were determined by the addition of coelenterazine, the cell-permeable substrate of *Renilla* luciferase, to a final concentration of 5 μM, and were then quantitated by a VictorLight luminescence/fluorescence plate reader (Perkin Elmer). The luciferase signal emitted by p62-RL-HEK treated with vehicle alone (0.1% DMSO) was referred to as 100% Relative Luc. Cells that are treated with either 3-MA (5 μM) or rapamycin (200 nM) were included as positive controls.

Our data demonstrated that p62-RL-HEK cells treated with 3-MA exhibited a significant increase of luciferase signal, which was an indicative of accumulation of p62 due to inhibition of autophagy by 3-MA. On the other hand, p62-RL-HEK cells treated with rapamycin exhibited a significant decrease in luciferase signal, consistent with the accelerated degradation of p62 resulted from rapamycin-elicited activation of autophagy. Herbal extract that induced greater alterations in Relative Luc as compared to that by 3-MA or rapamycin was identified as potential autophagy modulator.

Autophagic Activity Assay Using a GFP-LC3-Expressing Cell Line

HEK293 cells stably transfected with a GFP-tagged LC3 expression construct was generated and verified for the constitutive expression of the recombinant GFP-LC3. A single clone derived from a homogenous population of GFP-LC3-expressing HEK293 cells was isolated and named as GFP-LC3-HEK. To examine autophagy activity, GFP-LC3-HEK cells were seeded onto 6-well microplates and treated with various concentrations of BVEE for 24 hr. Respective treatments with 3-MA (5 μM) and rapamycin (200 nM) were included as positive controls. Clarified lysates derived from BVEE-treated cells were analyzed by SDS-PAGE and western blot using anti-p62, anti-LC3, and anti-GAPDH antibodies.

Neprilysin Activity Assay

SH-SY5Y cells were grown to confluence in 100 mm culture dishes, then were seeded in 12-well plates (1 mL; cell density $1\times10^6$ cells/mL). After plating for 1 day, the medium was replaced with fresh DMEM/F-12 supplemented with 10% FBS with or without the indicated compound (concentration from 0.25 to 30 μg/mL), then the cells were incubated for another 24 hr, after which the medium was replaced with 200 μL assay buffer (PBS containing 5.5 mM D-glucose, 0.3 mM sodium pyruvate, 25 mM sodium bicarbonate, and 1.5 μM zinc sulfate) containing 4 μM qf-Aβ(1-7)C and the cells were incubated for 1.5 hr. To measure Aβ-degrading activity, 150 μL of the assay buffer was taken for fluorescence measurement on a SpectraMax Gemini EM (Molecular Devices, USA) with excitation at 346 nm and emission at 442 nm.

Intracerebral Aβ42-Injection Mouse Model of AD

To generate the acute Aβ42-induced mouse model of AD, 8-wk old C57BL/6 male mice were intraperitoneally anesthetized with 40 mg/kg sodium pentobarbital, followed by the injection of aggregated Aβ42 into the dorsal hippocampus using a 26-gauge needle connected to a microsyringe (Hamilton). The coordinates of the stereotaxic surgery were as follows: 2 mm posterior to the bregma, 2.1 mm bilateral to the midline, and 1.8 mm ventral to the skull surface. The volume of injection was 1 μL of aggregated Aβ42 or 1 μL PBS. Mice subject to surgical procedures were allowed to recovery for 7 days. The Aβ42 aggregate was prepared from a solution of 10 mM of soluble Aβ42 in 0.01 M PBS, pH 7.4. The solution was incubated at 37° C. for 3 days to form the aggregated Aβ42 and stored at −70° C.

Cognitive Function Measurements of a Injection Mouse Model

The cognitive function of Aβ42-injection AD mice was assessed by Morris water maze. Briefly, Aβ42-injection AD mice were orally administered with either vehicle alone (0.1% DMSO) or 250 mg/kg BVEE daily for 2 months. C57BL/6 male mice receiving sham operation or intracerebrally injection of PBS were fed with vehicle alone and served as untreated controls. At the conclusion of dosing regime, mice were put into the water maze from 4 different quadrants, and the spatial memory of each mice was independently assessed by the average latency time each animal took to find the hidden platform. This cognitive functional test was consistently conducted during the last 4 hours of the day portion of the light cycle within a confined environment exposed to minimal disturbance. The spatial acquisition trial was conducted daily for 5 consecutive days.

Immunohistochemical (IHC) Analysis

To validate the anti-AD effects of BVEE that would not elicit significant neurotoxicity, the phenotypical changes of autophagy activation in brain of treated and control animals were determined by immunohistochemistry. Prior to being sacrificed, animals were perfused with 4% paraformaldehyde in 0.1 M phosphate buffer, pH 7.4. The brains were cryosectioned horizontally into 15 μm sections that were mounted on gelatin-coated slides, followed by incubation with a blocking-permeabilizing solution (5% donkey serum and 0.25% Triton X-100) for 1-3 h. BVEE-induced autophagy activation in animals were visualized by anti-p62 antibodies. Fluorescent signal was acquired by a laser confocal microscope (Leica TCS-SP5-MP).

Animal Experiment Using AD Double Transgenic Mice

All experiments protocols were approved by the Institutional Animal Care and Use Committee (IACUC) of Academia Sinica. APP/PS1 transgenic mice (B6C3-Tg (APPswe, PSEN1dE9) 85Dbo/Mmjax) and non-transgenic littermate controls were used in the following experiments. To stabilize the genetic background, the APP/PS1 mice were backcrossed with the wild-type (WT) C57BL/6J mice in the National Laboratory Animal Center. Genomic DNA of the APP/PS1 mice and the WT littermates were isolated by ZR Genomic DNA™ Tissue MiniPrep kit (Zymo Research Corp.). Human APPswe and PSEN1dE9 genes were then amplified by polymerase chain reaction (PCR). Primers for APPswe were 5'-AGGACTGACCACTCGACCAG-3' (SEQ ID NO: 1) and 5'-CGGGGGTCTAGTTCTGCAT-3' (SEQ ID NO: 2) while those for PSEN1dE9 were 5'-AATAGAGAACGGCAGGAGCA-3' (SEQ ID NO: 3) and 5'-GCCATGAGGCACTAATCAT-3' (SEQ ID NO: 4). Amplified DNA fragments were then visualized by 1.5% agarose gel electrophoresis with SYBR® Safe DNA Gel Stain (Invitrogen). Lyophilized BVEE powder (provided by Industrial Technology Research Institute, ITRI) was dissolved in N-Methyl-2-pyrrolidone (NMP) as the 10× BVEE stock (200 mg/mL), which was prepared twice a week and stored at 4° C. before dilution. The 10×BVEE stock were then diluted 10-folds with the pre-mixed kolliphor/saline solution (1:3.5, v/v) before the gavage administration. The APP/PS1 mice received 250 mg/kg/day of BVEE or saline treatment by gavage administration six days/week. Dosage was adjusted once a month according to the body weight, which was recorded once a month.

Evaluation of Long-Term BVEE-Treated APP/PS1 Mice on Cognitive Ability by Morris Water Maze Mice were subjected to the Morris water maze test at the age of 11 months. The apparatus of the Morris water maze consists three components: one water tank (100 cm diameter and 35 cm height), one transparent circular platform (10 cm diameter), and the TopScanLite tracking system (CleverSys Inc). One black triangle, red square, blue circle, and green star were respectively placed at the north, west, east and south side of the tank wall as visual cues. The tank was filled with water and milk, and therefore the transparent platform hidden 2 cm beneath the water surface was invisible. The submerged platform was placed in the quadrant 3 of the tank and kept in the same location during the spatial acquisition trial. The Morris water maze test was consisted of two trial phases: the spatial acquisition trial (Day 1 to Day 5, four trials per day) and the probe trial on Day 6.

Start positions for individual trial were selected semi-randomly as described in a previous study (Vorhees C V and Williams M T (2006) Nat Protoc 1(2):848-858). The mouse was gently placed in the start position and allowed to swim for 90 sec to find the hidden platform. The latency time was recorded if the mouse had reached the platform within 90 sec and stayed on the platform for 30 sec. Mouse failing to find the platform within 90 sec time limit was guided to the platform by putting an orange flag on the platform for an extra 30 sec. The mice who found the platform in this time period were allowed to stay on the platform for another 30 sec, while the mice who failed to find the platform were directly put on the platform for 30 sec. After finishing the trial, these mice could return to their home cage and then rest for at least 15 min until beginning of the next trial. Hair dryer and the tissue paper were used to keep the mouse warm and avoid hypothermia during the whole cognitive test. Twenty-four hours after the last day of the spatial acquisition trial, the platform was removed from the water tank for a one-day probe trial. Each mouse received a 60-sec trial and the spatial memory was evaluated by recording the latency time of the location of hidden platform.

ELISA

After the Morris water maze test, five to seven mice from each group were sacrificed and their hippocampus, cerebral cortex were collected, aliquoted and stored at −80° C. for subsequent ELISA assay. Collected brain samples were homogenized in 400 µL TBS buffer (50 mM Tris, 2 mM EDTA, 150 mM NaCl, protease inhibitor cocktail (Sigma P8340), pH 7.4) with 1 mL Duall tissue grinder with PTFE pestle and centrifuged at 4° C. for 20 min at 15000 rpm (20000×g). The insoluble pellet fractions were collected and then resuspended in 400 µL 70% formic acid, sonicated for 1 min, and centrifuged at 4° C. at 15,000 rpm (20000×g) for another 20 min. Supernatant were equilibrated (1:20) with neutralization buffer (1 M Tris, 500 mM $Na_2HPO_4$), aliquoted and collected as the "insoluble Aβ fraction".

Insoluble human Aβ40 and Aβ42 levels of the collected hippocampus and cerebral cortex were quantified by commercial human Aβ40 (KHB3482, Invitrogen) and Aβ42 (KHB3442, Invitrogen) ELISA Kit. Aβ40 and Aβ42 detections were conducted according to manufacturer's instructions. Total protein concentration of the insoluble Aβ fractions was quantified by the Bradford method. The insoluble Aβ fractions were then diluted at the ratio of 1:500 and 1:1,000 for Aβ40 and Aβ42 detection, respectively. Diluted insoluble Aβ fraction and primary detection antibody were added into wells and incubated at room temperature for 3 hours with shaking. After washing, horseradish peroxidase (HRP)-conjugated secondary antibody solution was supplied at room temperature for 30 min with gentle agitation. Stabilized chromogen solution for Aβ40 and Aβ42 detection was added at room temperature for 30 min and 15 min, respectively. Reactions were terminated by the stop solution, and the absorbance at 405 nm was measured immediately.

ThS Staining

After the Morris water maze test, three mice of each group were euthanized by cervical dislocation. Three mice were perfused with PBS (136.89 mM NaCl, 2.68 mM KCl, 1.62 mM $KH_2PO_4$, and 10.14 mM $Na_2HPO_4$, pH 7.4) buffer and 4% paraformaldehyde (PFA)/PBS. Perfused mice brain were then post-fixed in 4% PFA/PBS with gentle shaking at room temperature for another 24 hours. After post-fixation, brain samples were wash with PBS buffer and preserved in 70% ethanol/water solution until the paraffin embedding protocol.

PFA-fixed brain tissues were dehydrated by a semi-enclosed benchtop tissue processor (Leica TP1020). Paraffin blocks containing the dehydrated brain samples were prepared by Leica EG1150 H. Coronal sections with 3 µm thickness were cut on a rotary microtome (Leica RM2235). Two brain sections were picked up with a paint brush, put onto the surface of a water bath, floated onto the surface of clean glass slides, and placed on a 34° C. warming block for several hours.

Paraffin slides were de-paraffinized and rehydrated with xylene, absolute ethanol, 95% ethanol, 70% ethanol and water, sequentially. Rehydrated slides were applied with 1% (w/v) thioflavin S solution for 10 min at room temperature protected from light. Wash the slides with 80% ethanol and water to remove excess fluorochrome and facilitate visualization. Thioflavin S-positive signals were then visualized in a fluorescence microscope, equipped for evaluation of green fluorescence and the plaque number, plaque area and plaque size were analyzed by ImageJ.

Liver and Kidney Toxicity Test

Blood samples were collected through the orbital sinus before euthanasia. Collected blood samples were incubated on ice for at least an hour, and centrifuged at 1500×g for 10 min (4° C.). Supernatant serum samples were collected, aliquoted and frozen in −30° C. Serum aspartate transaminase (AST), alanine transaminase (ALT), alkaline phosphatase (ALP), blood urea nitrogen (BUN) and creatinine (CRE) were then analyzed by Fuji Dri-chem 4000i Analyzer (Taiwan Mouse Clinic).

Example 1 *Bauhinia* Extract Decreases Tauopathy Induced Toxicity

In this example, the effect of the ethanol extract of *Bauhinia variegate* (BVEE), which was prepared in accordance with the procedures set forth in "Materials and Methods" section, on tauopathy toxicity was evaluated by monitoring the expression of GFP-hTau fusion protein in zebrafish embryo. The zebrafish embryos at 1-cell stage was injected with the expression construct pHuc-hTau-GFP, the expression of the Tau protein was then monitored by the co-expressed GFP signal. Using fluorescence microscope, GFP-labeled neuronal cells were observed at 24, 48 and 72 hpf. Neuronal numbers with GFP signals in embryos at 72 hpf were counted and separated into two groups: lower than 2 neurons (0-2), and more neurons between 3-5. Results are illustrated in FIG. 1.

Without BVEE treatment, 77% of embryos had 0-2 neurons and only 23% embryos with more neurons between 3-5. Conversely, BVEE treatment decreased tauopathy induced toxicity by increasing neuron expression in zebrafish embryos to 43% (FIG. 1, panel B).

Example 2 Bauhinia Extract Promotes Neurite Outgrowth

Similar to example 1, zebrafish embryo at 1-cell stage was injected with the expression plasmid pHuC-hTau-GFP, then treated with BVEE or DMSO (the control) to see if BVEE may promote neurite outgrowth by counting the number of sprouting neurons. Results are illustrated in FIG. 2.

Figure 2:
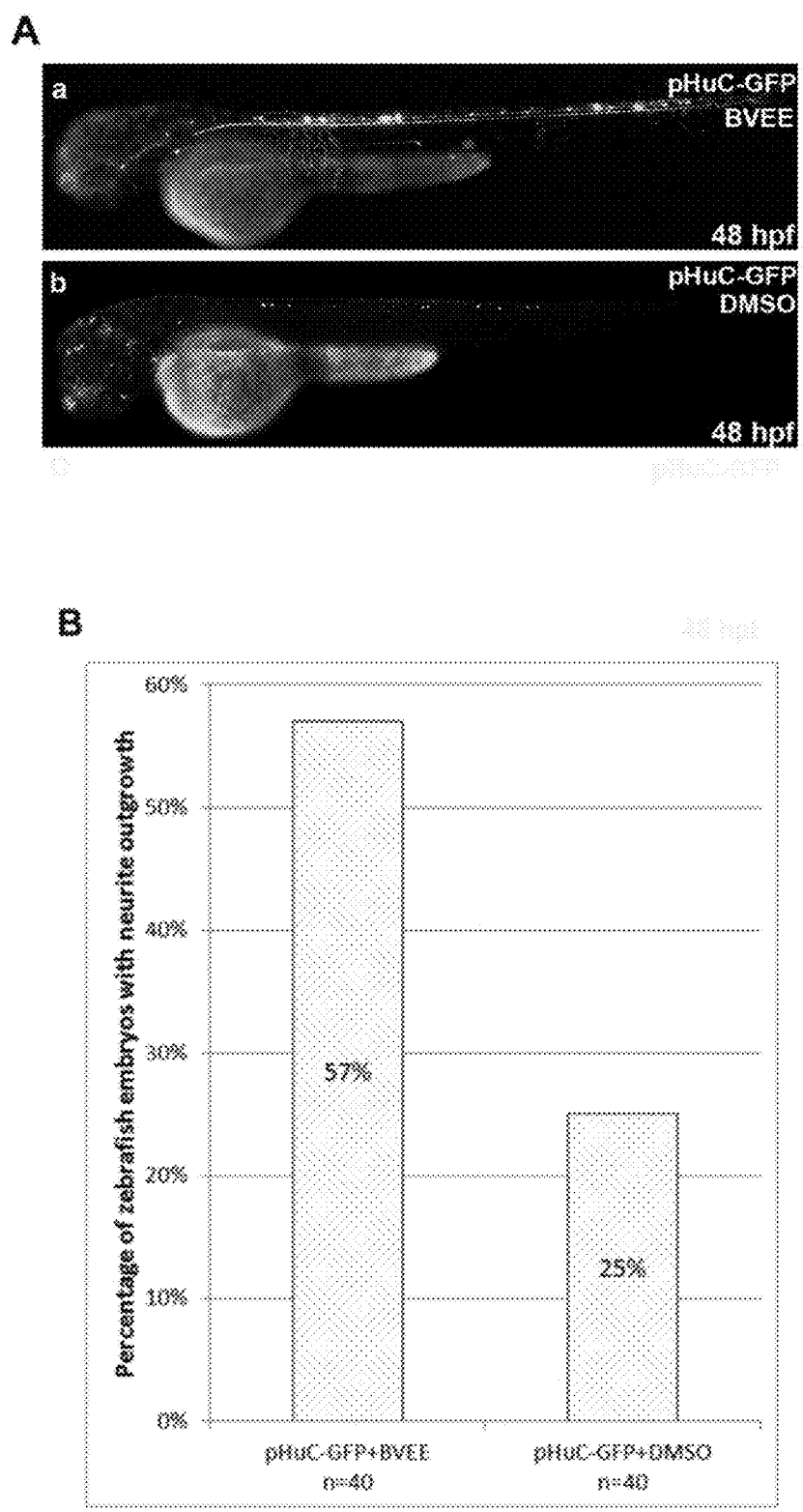
FIG. 2. Treatment with BVEE induces the promotion of neurite outgrowth in zebrafish embryo. A. The expression plasmid pHuC-GFP was first injected into zebrafish embryos at one-cell stage. Eight hours after injection, those injected embryos were treated with BVEE or DMSO as control. B. zebrafish numbers with significant neurite outgrowth were counted 40 hrs after treatment.

As the data indicated, HuC promoter-driven GFP was expressed in trigeminal ganglia, axons, and interneurons of zebrafish embryos at 48 hpf (FIG. 2, panel A). The percentage of injected zebrafish embryos treated with DMSO with neurite outgrowth was 25% (FIG. 2, panel B). Conversely, BVEE treatment induced significant neurite outgrowth, in which the percentage of zebrafish embryo with neurite outgrowth reached a significant high level of 57% (FIG. 2, panel B).

Example 3 Effect of BVEE on the Activation of Autophagy

In this example, the ability of BVEE to induce autophagy was examined by monitoring the conversion of LC3-I to LC3-II and the expression level of p62 in cells treated with or without BVEE. Results are summarized in FIG. 3.

Figure 3:
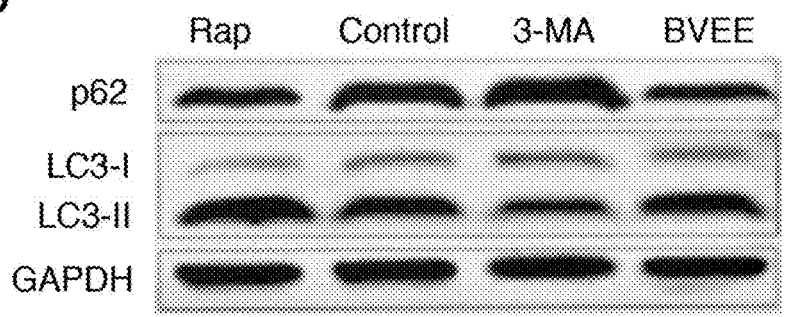
FIG. 3. Treatments with BVEE induces autophagy. A. GFP-LC3-HEK cells were treated with BVEE (50 µg/ml) at 37° C. for 24 h. An autophagy inducer, rapamycin, and an autophagy inhibitor, 3-MA, were included as controls. Clarified lysates containing equal amounts of proteins were resolved by SDS-PAGE and analyzed by Western blotting with anti-p62 (top panel), anti-LC3 (middle panel), and anti-GAPDH (bottom panel) antibodies. B. A stable cell line p62-RL-HEK that overexpresses *Renilla* luciferase-tagged p62 was treated with BVEE (50 µg/ml) at 37° C. for 24 h. Additional treatments with either rapamycin or 3-MA were included as controls. *Renilla* luciferase signal was determined by the addition of coelenterazine at equal volume to a final concentration of 5 µM. Luminescence emitted by DMSO-treated cells (Control) was referred to as 100% relative *Renilla* luciferase signal.
Figure 3:
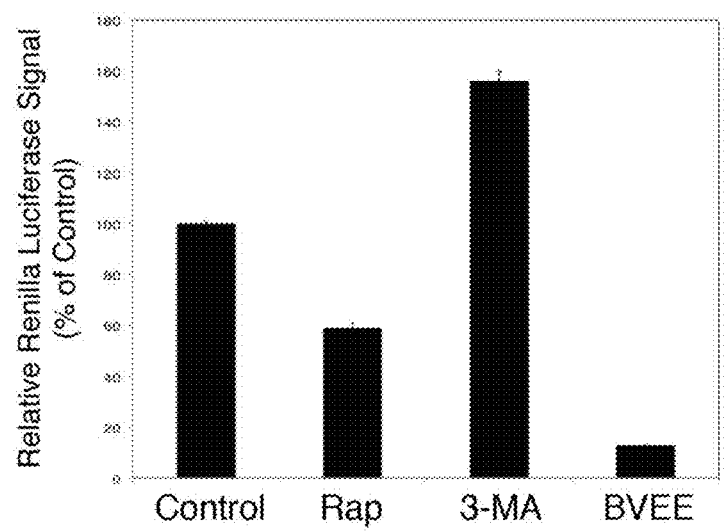

FIG. 3, panel A is a western blot analysis of the expression of LC3-I, LC3-II and p62. The data indicated that BVEE-treated cells exhibited significant increases in the level of LC3-II, concomitant with a significant decrease in that of p62. Consistently, BVEE treatments also resulted in a dramatic reduction in p62 in a cell-based luciferase reporter assay of autophagy activity (FIG. 3, panel B). These data strongly suggest that BVEE of the present disclosure contains active ingredients that activate autophagy.

Example 4 Effect of BVEE on Neprilysin (NEP) Activity

In this example, the effect of BVEE on NEP activity was examined by monitoring the level of a peptide substrate, qf-Aβ(1-7)C peptide, in which a fluorophore and a quencher are respectively linked to its C-terminus and N-terminus. The existence of the quencher quenches the fluorescence. When qf-Aβ(1-7)C is cleaved by NEP, the quencher and the fluorophore are separated and strong fluorescence is emitted from the fluorophore. NEP is a type II membrane protein, and if the membrane of the cells (e.g., SH-SY5Y or N2a cells) contained higher amounts of NEP, then higher amounts of qf-Aβ(1-7)C peptides would be digested and thereby resulting higher fluorescence intensity. Results are illustrated in FIG. 4.

Figure 4:
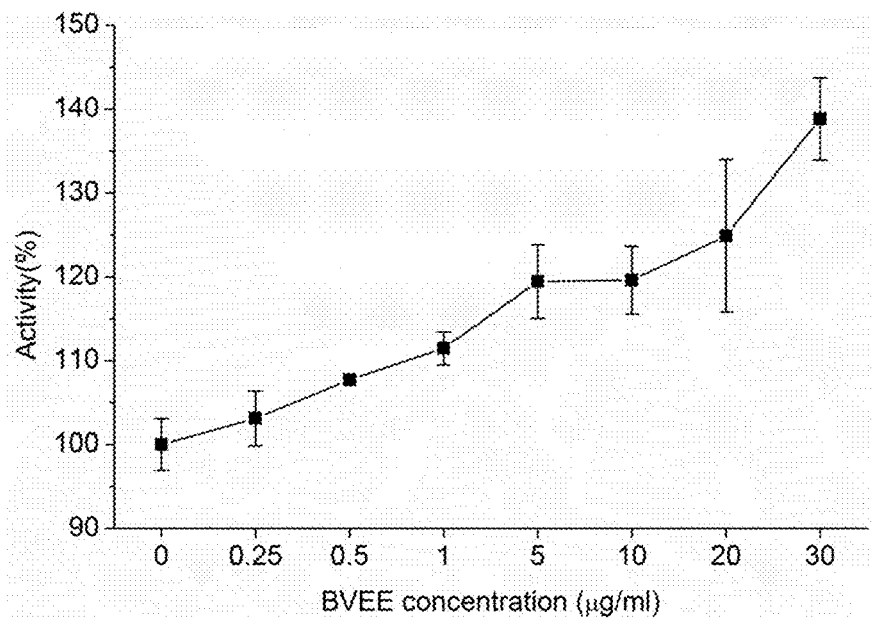
FIG. 4. Effect of BVEE on NEP activity. The line graph illustrates the dose dependency of BVEE on NEP activity in accordance with one embodiment of the present disclosure.

As evident from FIG. 4, there is a clear dose-dependency between the NEP activity and BVEE concentration, for NEP activity increases as the concentration of BVEE increase, suggesting that BVEE treatment may promote NEP-dependent clearance of Aβ.

Example 5 BVEE does not Elicit any Significant Cytotoxicity

In this example, the toxicity of BVEE preparation of the present disclosure was determined by use of a cell viability assay. Results are provided in FIG. 5.

Figure 5:
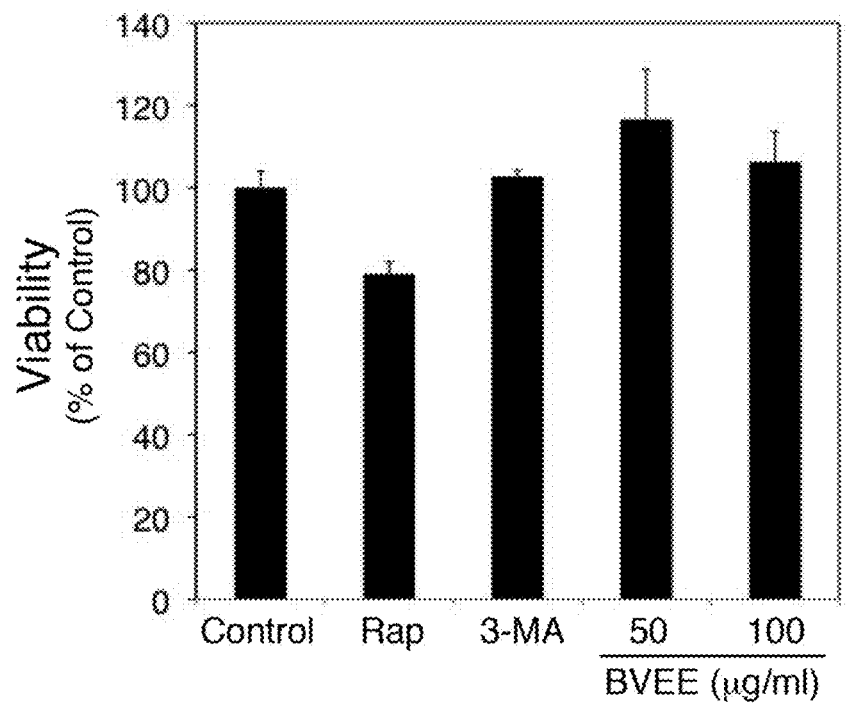
FIG. 5. The viability of p62-RL-HEK cells in response to BVEE treatment. The p62-RL-HEK cells were treated with or without BVEE (50 or 100 µg/ml) at 37° C. for 24 h. Additional treatments with either rapamycin or 3-MA were included as references. Viable cells was determined by the addition of CellTiter 96 AQueous non-radioactive cell proliferation assay reagents as described in Methods. Absorbance at 490 nm by DMSO-treated cells (Control) was referred to as 100% relative viability.

As depicted in FIG. 5, cell viability remained relatively comparable to that of the control in cells treated with either low (50 μg/mL) or high concentration (100 μg/mL) of BVEE. The result clearly indicated that BVEE of the present disclosure does not possess any toxicity toward p62-RL-HEK cells, thus is safe to use as a dietary supplement.

Example 6 BVEE Treatment Induced Cognitive Improvement in an Intracerebral Aβ42-Injection Mouse Model of AD In this example, the efficacy of BVEE of the present disclosure on cognitive improvement was evaluated in an acute Aβ42-induced AD mouse model in accordance with procedures described in "Materials and Methods" section. Results are summarized in FIGS. 6 and 7.

Figure 6:
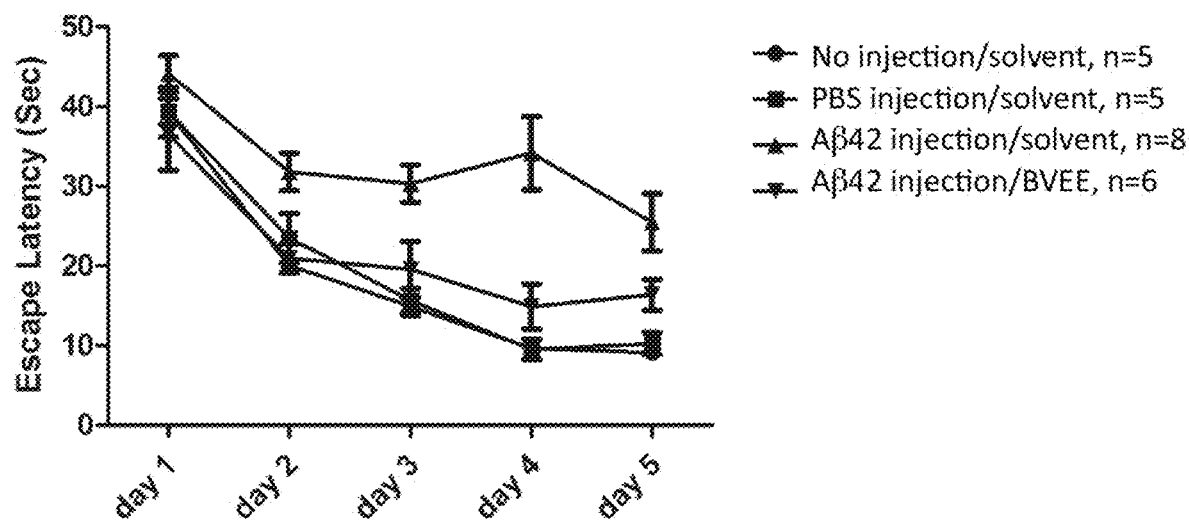
FIG. 6. Aβ42-injected AD mice receiving BVEE exhibit cognitive improvement. AD mice treated with BVEE can remember the location of hidden platform comparable to the performance of control mice (escape latency) in Morris water maze test. Non-operation mice (No injection/solvent), n=5; Sham-operated mice treated with solvent (PBS injection/solvent), n=5; Aβ42-injected mice treated with solvent (Aβ42 injection/solvent), n=8; Aβ42-injected mice treated with BVEE (Aβ42 injection/BVEE), n=6.
Figure 7:
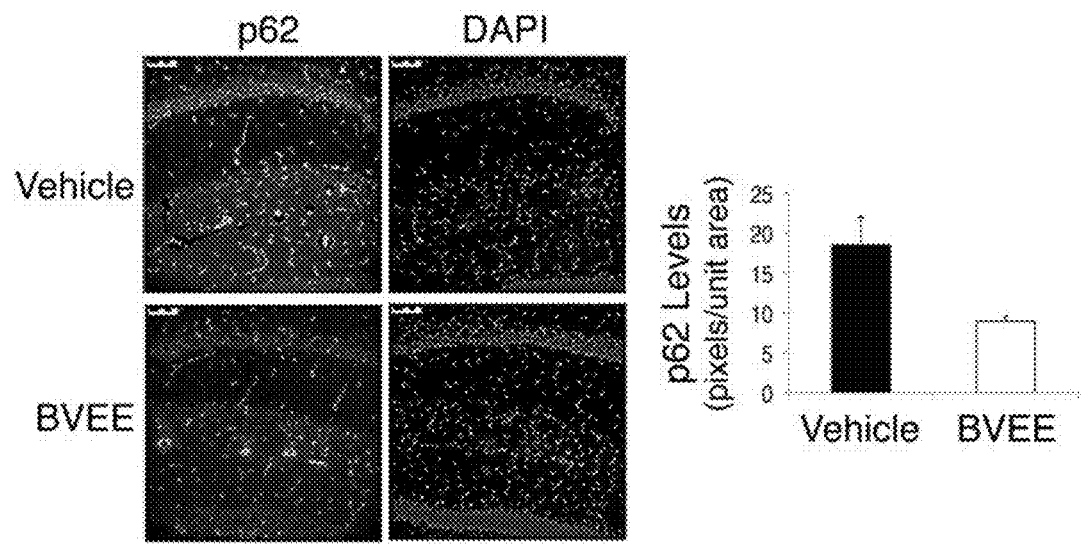
FIG. 7. BVEE induces activation of autophagy in hippocampus of Aβ42-injected mice. Male C57BL/6 mice were intracerebrally injected with Aβ42 and treated with vehicle alone (0.1% DMSO) or BVEE (250 mg/Kg/d) for 2 months. After the cognitive function of mice were analyzed by Morris water maze test, brains of mice were then processed for fluorescence immunohistochemistry analysis with anti-p62. DAPI staining was performed to visualize nucleus. Representative images of fluorescence immunohistochemical analysis show the levels of p62 (red) and DAPI staining (blue) in the hippocampal region of BVEE-treated and untreated mice (vehicle). Quantitative data are shown as average p62 levels (±SD) from 3 consecutive sections (15 µm thick) of mouse brain (n=3).

As evident from FIG. 6, significant cognitive improvement was found in Aβ-injected mice treated with BVEE, whereas those treated with vehicle alone displayed a marked cognitive deficit as compared to sham-operated animals. Consistently, a dramatic increase in the induction of autophagy was found in the hippocampus of mice treated with BVEE, which was evidenced by a significant decrease in the expressed level of p62 (FIG. 7).

Taken together, the findings support the proposition that BVEE of the present disclosure contains active ingredients that activate autophagy, which in term suppresses Aβ42-elicited neurotoxicity and improves spatial learning and memory of the test animals.

Example 7 Effect of BVEE on AD Double Transgenic Mice

In this example, effect of BVEE on the spatial and reference memory of the test animals (i.e., APP/PS1 mice) were evaluated by the Morris water maze test in accordance with the procedures described in "Materials and Methods" section. Results are summarized in FIG. 8.

Figure 8:
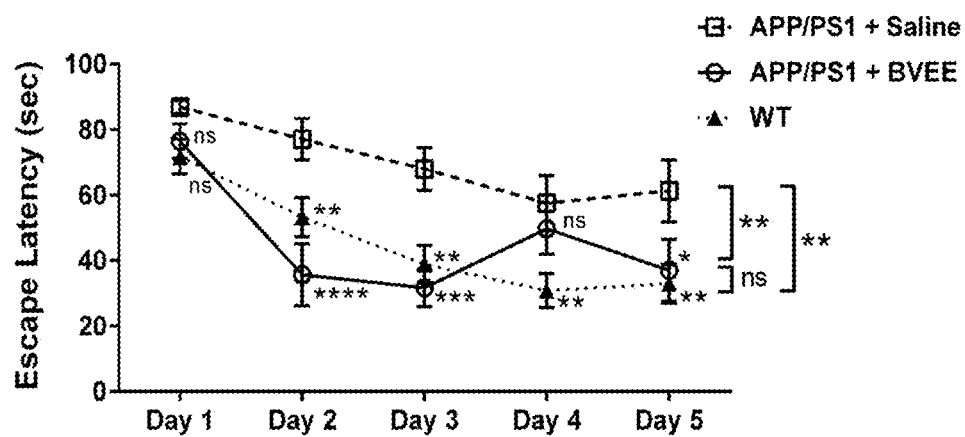
FIG. 8. Long-term BVEE treatment improved the cognitive status of the APP/PS1 transgenic mice. 3-month-old APP/PS1 mice were orally treated with 250 mg/Kg·BW BVEE or saline 6 times a week for 7 months. Spatial and reference memories of the saline-treated APP/PS1 mice (n=12), BVEE-treated APP/PS1 mice (n=8) and WT littermates (n=15) were then assessed by (A) spatial acquisition trials and (B) probe trial of Morris water maze test at 10 months of age. Data was expressed in mean±SEM. Significance between different treatment groups calculated by two-way ANOVA with Fisher's LSD test are shown at the right side of the curves. Data of the WT group and the BVEE-treated group on each day were compared with the saline-treated APP/PS1 mice. * $P<0.05$,  $P<0.01$, * $P<0.001$, **** $P<0.0001$, ns, not significant.
Figure 8:
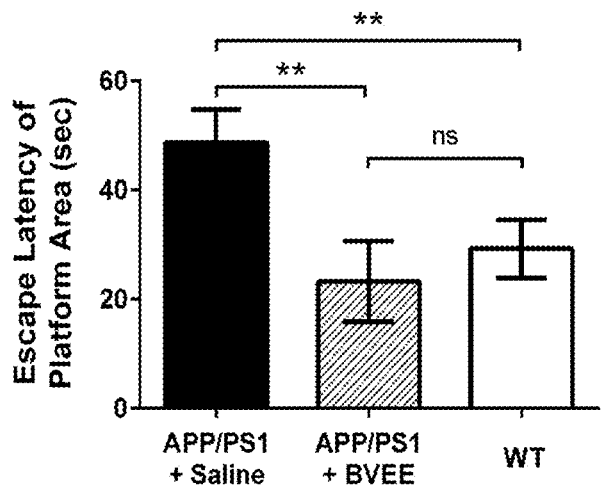

On the first day (Day 1, FIG. 8), the APP/PS1 mice received both saline or BVEE treatment exhibited similar escape latencies in reaching the platform as the WT littermate, which indicated that these mice had similar learning ability and no quadrant preferences after the BVEE treatment. Conversely, the saline-treated APP/PS1 mice demonstrated impaired performances with longer escape latencies to locate the hidden platform. 75% of the mice in this group (9 out of 12 mice) were unable to locate the hidden platform on the first day of the test. After five days of successive trainings, some of the APP/PS1 mice were able to reach the platform within the 90 sec time limit, yet their escape latencies remained at about 60 sec. On the other hand, the WT mice, which did not develop AD symptoms during their lifespan, quickly learned to locate the platform after the second trial on Day 1 (12 out of 16 mice). Significant decline of escape latencies between the WT and APP/PS1 mice were observed after Day 2. Furthermore, 94% of the WT mice (15 out of 16 mice) were able to locate the platform within 33 sec after finishing the spatial acquisition trials. Compared with the saline treatment group, mice receiving BVEE treatment exhibited remarkable cognitive improvement after five days of successive training (P<0.01), their escape latencies (i.e., BVEE-treated APP/PS1 mice) on Days 2 and 3 decreased significantly by 50%. Although the latency increased on Day 4, yet it was still lower than that of the saline-treated APP/PS1 mice. On day 5, the escape latency of the BVEE-treated mice were similar to that of the WT mice, and was significantly shorter than that of the saline-treated APP/PS1 mice. After finishing the 5-day spatial acquisition trial, mice were subjected to a one-day probe trial, which was used to evaluate whether they had learned to locate the platform by recording the escape latencies, results are depicted in FIG. 8, panel B. Similar to the results found in the spatial acquisition trial, the saline-treated mice exhibited impaired cognitive capability in the probe trial (about 50 sec). Conversely, the BVEE-treated mice exhibited similar cognitive ability as that of the WT littermate.

Figure 9:
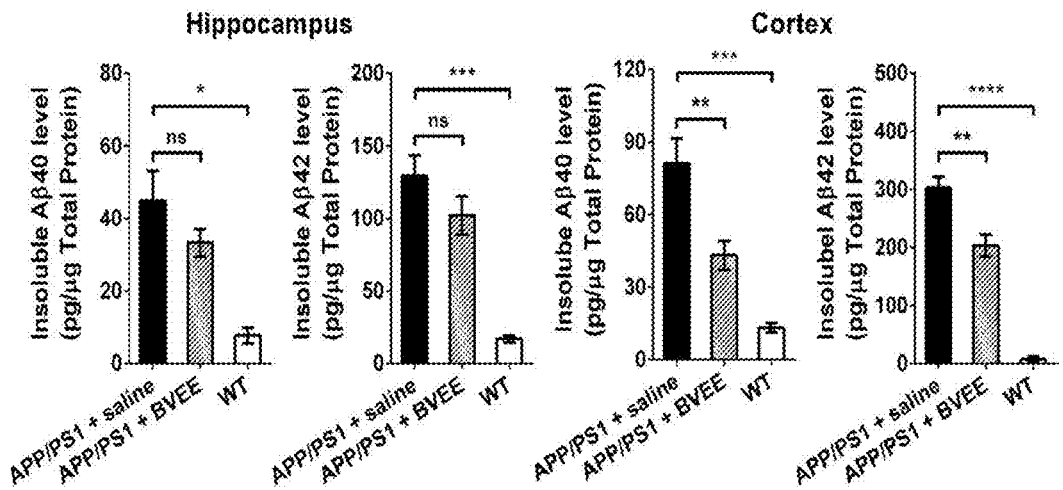
FIG. 9. Amyloid plaque burdens of APP/PS1 mice were decreased after BVEE treatment. Plaque burdens of the 11-months-old WT littermate, saline-treated and BVEE-treated APP/PS1 mice were assessed by (A) ELISA and (B) thioflavin S staining. (A) After euthanasia, cerebral cortex and hippocampus were isolated for ELISA. Insoluble human Aβ40 and Aβ42 levels were quantified by commercial ELISA kit (n=6 for BVEE treatment; n=5 for saline treatment; n=3 for WT mice). (B) Plaque burdens were further visualized by thioflavin S staining. Scale bar represents 800 µm. (C) Plaque number, total plaque area, and percentage covered by plaques per ThS-stained section were quantitated by ImageJ. Data was expressed in mean±SEM. Significant and not-significant (ns) results compared with the saline-treated APP/PS1 mice were demonstrated. * $P<0.05$,  $P<0.01$, * $P<0.001$, **** $P<0.0001$ were calculated by one-way ANOVA with Fisher's LSD test (n=12 sections from 2 mice with BVEE treatment; n=40 sections from 7 mice with saline treatment; n=10 sections from 5 WT mice).
Figure 9:
Figure 9:
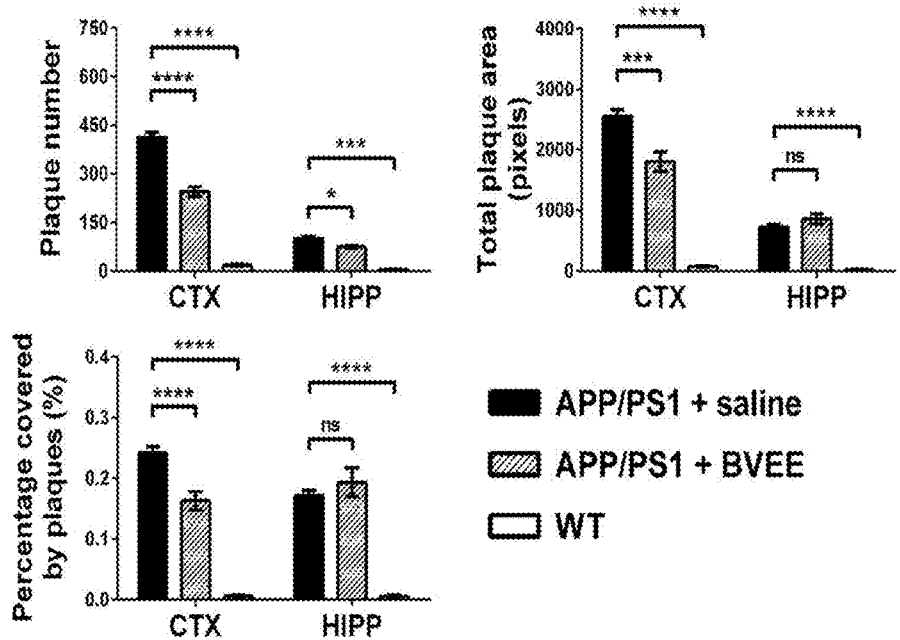

After finishing the cognitive test, the APP/PS1, BVEE and WT mice were euthanized at 11 months of age, and the insoluble human Aβ40 and Aβ42 levels of the hippocampus and cerebral cortex were quantified by ELISA. Results are illustrated in FIG. 9, panel A. Abundant Aβ40 and Aβ42 plaques were found in both hippocampus and cerebral cortex of the saline-treated APP/PS1 mice, as compared to that of the WT mice. Minor decline of the β-amyloid deposits in hippocampus were observed (25% decrease in Aβ40 and 21% decrease in Aβ42) after the BVEE-treatment, which had been administered for 8 months. On the other hand, the insoluble Aβ40 and Aβ42 deposits in the cerebral cortex were remarkably reduced by 46% and 33%, respectively (P<0.01). Consistent to this finding, marked reduction in amyloid plaques quantified by ThS staining was also found in cortex, and significant decrease in plaque number was observed in hippocampus (FIG. 9, panels B and C).

Example 8 Effect of BVEE Treatment on the Function of Liver or Kidney

In this example, long term effect (i.e., 8-month) of BVEE on the test animals were evaluated by monitoring their liver and kidney functions. Liver function was determined by measuring the serum levels of various metabolic enzymes, which include aspartate transaminase (AST), alanine transaminase (ALT) and alkaline phosphatase (ALP); whereas the renal function was determined by measuring the serum levels of blood urea nitrogen (BUN) and creatinine (CRE). Results are depicted in FIG. 10.

Figure 10:
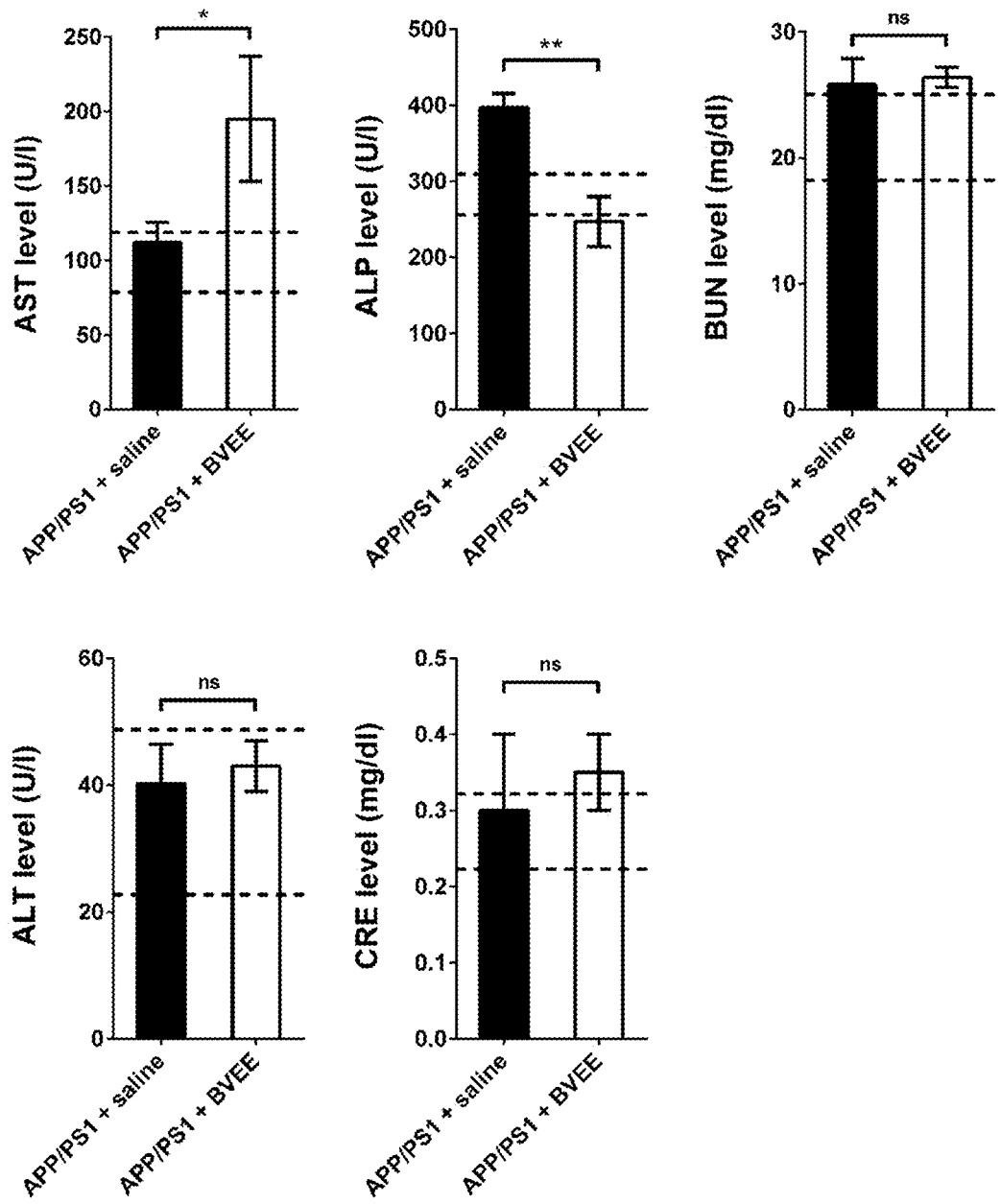
FIG. 10. Liver and kidney toxicity test for the long-term BVEE treatment. Blood samples of the BVEE-treated APP/PS1 mice were collected, and AST, ALT, ALP, BUN, CRE levels were then analyzed. All results were expressed in mean±SEM (n=3 for BVEE treatment; n=4 for saline treatment). * $P<0.05$, compared with saline-treated APP/PS1 mice were calculated by ANOVA with Fisher's LSD test. Not significant; ns. The range of AST, ALT, ALP, BUN, CRE levels obtained from 10-wk-old ICR mice (n=10) are shown in dash line.

The data in FIG. 10 indicated that BVEE treatment did not significantly affect any of the ALT, BUN and CRE levels. However, a significantly higher level of AST and a significantly lower level of ALP were found in BVEE treated animals, as compared with those of the saline-treated control. Yet, none of the BVEE-treated animals exhibited pathological symptoms. Thus, we concluded that long-term BVEE oral administration for at least 8-months would not affect the liver and/or kidney functions of the test animals.

Example 9 Comparison of the Efficacy of Present Extracts on NEP Activity and Autophagy Induction In this example, the efficacy of the present extracts of Bauhiniaxblakeana Dunn. on NEP activity was examined. The extracts were prepared in accordance with the procedures described above in the "Materials and Methods" section, in which 95% ethanol, 40% ethanol or hot water was used as the solvent to extract stem powders of Bauhiniaxblakeana Dunn. Results are illustrated in FIG. 11.

Figure 11:
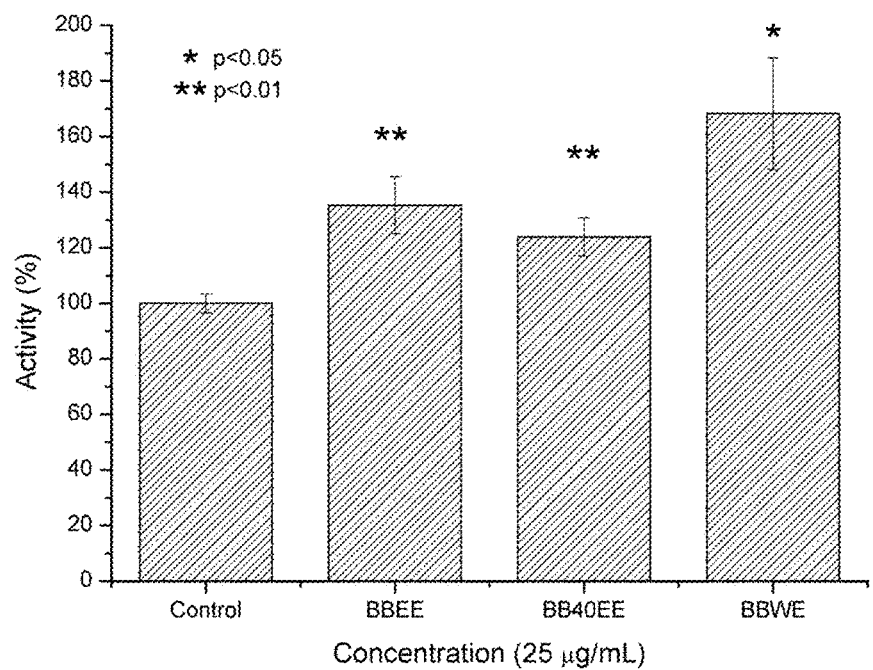
FIG. 11. NEP activity assay. This bar graph illustrates the respective effects of extracts of *Bauhinia×blakeana* Dunn. (BB) prepared by 95% ethanol, 40% ethanol, and water on NEP activity in accordance with one embodiment of the present disclosure.

As evidenced in FIG. 11, the extracts of Bauhiniaxblakeana Dunn. prepared by extraction with 95% ethanol (BBEE), 40% ethanol (BB40EE), or hot water (BBWE) exhibited increased NEP activity than that of the control.

Example 10 Effects of the Present Extracts Obtained by Various Types of Solvents on the Induction of Autophagy In this example, the efficacy of the present extracts of B. variegate on the induction of autophagy in p62-RL-HEK cells were examined, in which the extracts were respectively obtained by use of extracting solvents that include hexane, ether, ethyl acetate (EA), hot water and 95% ethanol. The present extracts of B. variegate were prepared in accordance with the procedures described above in the "Materials and Methods" section. Results are summarized in FIG. 12.

Figure 12:
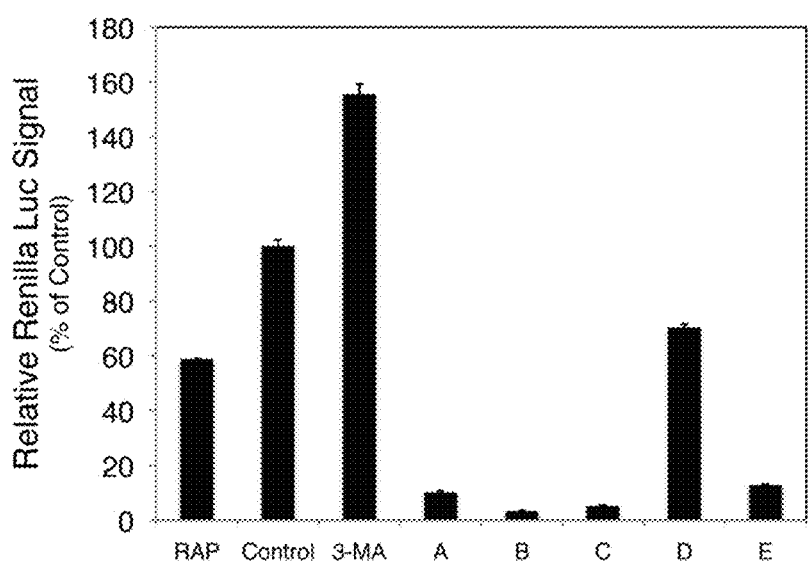
FIG. 12. The autophagy-inducing potency of extracts derived from *B. variegate* (BV) by using different solvents.

The data indicated that, while all the solvents could successfully extract the autophagy-inducing components from B. variegate, preferably, the autophagy-inducing constituents was isolated by use of organic solvents, such as hexane, ether, ethyl acetate, or ethanol (FIG. 12). These results suggest that the active ingredients of B. variegate can be efficiently isolated in an ethanol-based to extraction procedure, which might be conducive to the formulation of BVEE as a dietary supplement.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method for manufacturing a *Bauhinia* spp. extract, comprising the steps of:
    extracting a powdered stem of *Bauhinia* spp. with water or ethanol or 95% ethanol at a ratio from 1:5 (w/v) to 1:20 (w/v) at about 10-100° C. for about 0.5 hours to 10 days to produce the *Bauhinia* spp. extract.

2. The method of claim 1, wherein the powdered stem of *Bauhinia* spp. is extracted with water at the ratio of 1:10 (w/v) at about 50° C. for about 2 hours.

3. The method of claim 1, wherein the powdered stem of *Bauhinia* spp. is extracted with 95% ethanol (vol %) at about 15-35° C. for about 1-10 days.

4. The method of claim 3, wherein the powdered stem of *Bauhinia* spp. is extracted with 95% ethanol (vol %) at the ratio of 1:10 (w/v) at about 25° C. for about 7 days.

5. The method of claim 1, wherein the *Bauhinia* spp. is *Bauhinia variegate* or *Bauhinia*×*blakeana* Dunn.

* * * * *